United States Patent
Heuft et al.

(10) Patent No.: US 6,443,004 B1
(45) Date of Patent: Sep. 3, 2002

(54) METHOD AND DEVICE FOR DETERMINING THE FILLING LEVEL IN CONTAINERS

(75) Inventors: Bernhard Heuft, Burgbrohl; Hans-Ulrich Goller, Bonn-Bad Godesberg, both of (DE)

(73) Assignee: Heuft Systemtechnik GmbH, Burgbrohl (DE)

( * ) Notice: Subject to any disclaimer, the term of this patent is extended or adjusted under 35 U.S.C. 154(b) by 0 days.

(21) Appl. No.: 09/673,589

(22) PCT Filed: Apr. 27, 1999

(86) PCT No.: PCT/EP99/02828

§ 371 (c)(1),
(2), (4) Date: Oct. 18, 2000

(87) PCT Pub. No.: WO99/56094

PCT Pub. Date: Nov. 4, 1999

(30) Foreign Application Priority Data

Apr. 27, 1998 (DE) .......................... 198 18 768

(51) Int. Cl.⁷ ...................... G01F 23/28; G01F 23/296
(52) U.S. Cl. ................... 73/290 V; 73/290 R
(58) Field of Search .......................... 73/290 V, 290 R; G01F 23/296, 23/28

(56) References Cited

U.S. PATENT DOCUMENTS

| | | | |
|---|---|---|---|
| 3,802,252 A | | 4/1974 | Hayward et al. |
| 4,480,468 A | | 11/1984 | Sinha |
| 4,535,627 A | * | 8/1985 | Prost et al. ............ 73/290 B |
| 4,811,595 A | | 3/1989 | Marciniak et al. |
| 5,353,631 A | | 10/1994 | Woringer et al. |
| 5,528,933 A | | 6/1996 | Nemirow |

FOREIGN PATENT DOCUMENTS

| | | | |
|---|---|---|---|
| DE | 27 16 833 A1 | | 10/1977 |
| DE | 40 04 965 A1 | | 8/1991 |
| DE | 40 08 135 A1 | | 8/1991 |
| DE | 41 00 338 A1 | | 9/1991 |
| DE | 197 11 093 A1 | | 3/1998 |
| DE | WO 99/10722 | * | 8/1999 |
| EP | 0 831 308 A2 | | 3/1998 |
| GB | 2 293 450 A | | 3/1996 |
| GB | 2 298 279 A | | 3/1996 |
| WO | WO 94/24256 A1 | | 10/1994 |

* cited by examiner

*Primary Examiner*—Daniel S. Larkin
*Assistant Examiner*—André K. Jackson
(74) *Attorney, Agent, or Firm*—Gardner Carton & Douglas

(57) ABSTRACT

To ascertain the fill level of vessels (10), mechanical vibrations are produced in a vessel wall (30) and the vibration pattern is analysed. The vibration is produced in a vessel wall (30) which is contacted by the contents to an extent which varies depending on the fill level, and the vibration pattern is then evaluated to discover to what extent the vessel wall (30) is contacted on the inside by the contents. For this, the decay time, the frequency, the intensity and/or the time integral of the intensity can be evaluated or the site of the maximum intensity of the mechanical vibrations in the vessel wall can be ascertained.

7 Claims, 2 Drawing Sheets

METHOD AND DEVICE FOR DETERMINING THE FILLING LEVEL IN CONTAINERS

Figure 1:
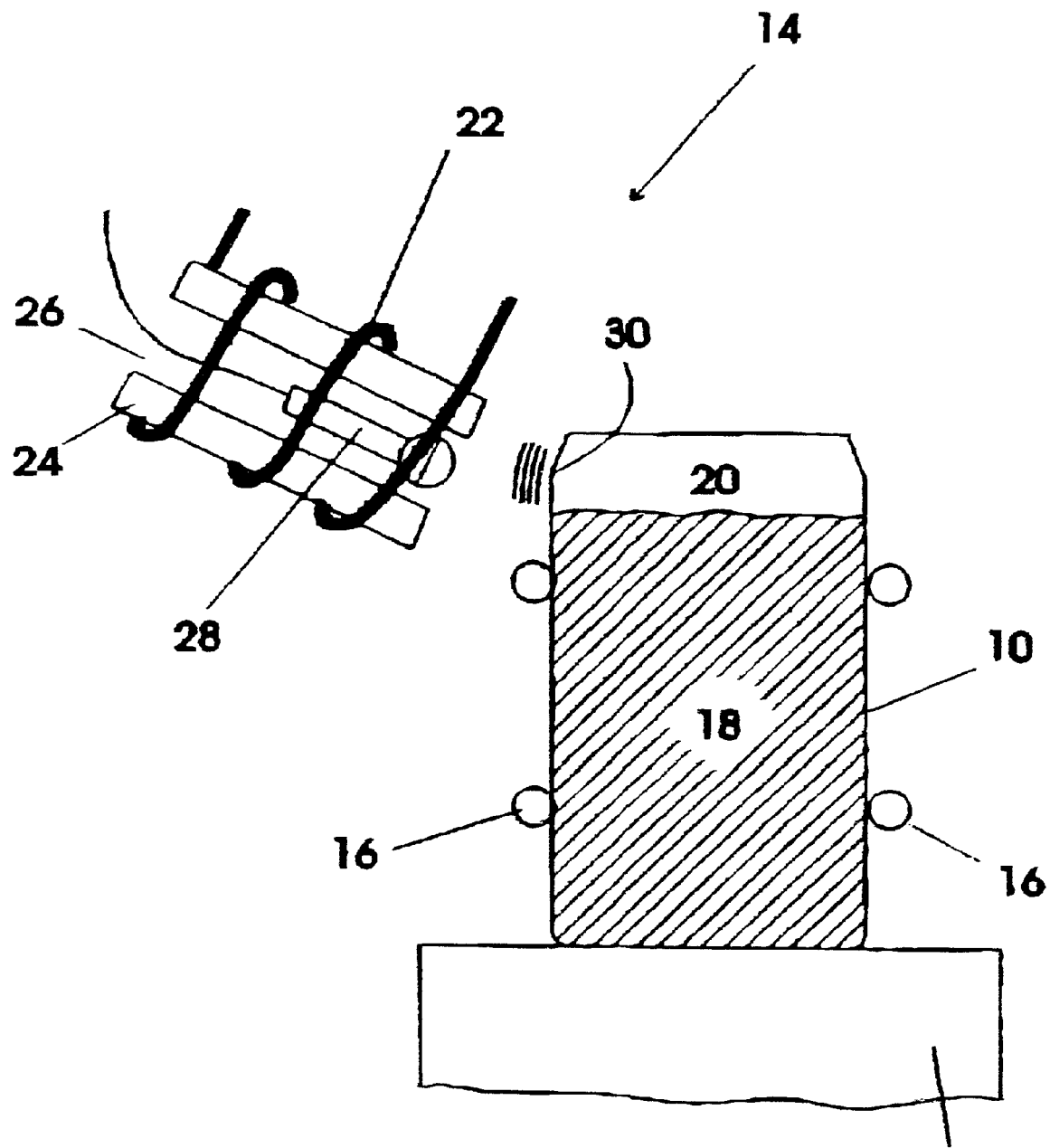

The invention relates to a method and a device for ascertaining the fill level in vessels, wherein mechanical vibrations are produced without contact in a vessel wall, the produced mechanical vibrations are recorded without contact and the recorded vibrations are analyzed.

Such a method is known from GB 2 298 279 A, based on the finding that, in gas vessels of a certain type, it is not the resonance frequency, but only the frequency amplitude, that changes depending on the contained residual amount. To establish the residual amount, sound waves of this resonance frequency are therefore directed onto the vessel by means of a loudspeaker and the intensity of the reflected sound waves of this frequency, is ascertained and compared with a threshold value.

It is known from DE 40 04 965 A1 to test vessels for the tightness of attached below-atmospheric pressure closures, by producing mechanical vibrations without contact in the below-atmospheric pressure closure by a short time magnetic field and evaluating the produced vibration with regard to frequency, duration and/or attenuation.

It is known from U.S. Pat. No. 3 802 252, U.S. Pat. No. 4 811 595, U.S. Pat. No. 5 353 631 and GB-A-2 293 450 to ascertain the internal pressure of a vessel by mechanically or magnetically impacting a vessel wall and measuring the resonance frequency of the vessel, from which the internal pressure is then derived.

A method for establishing a minimum and maximum fill level is known from DE-A-40 08 135 in which the resonance frequency is ascertained in each case at a certain point on the external wall of the vessel. Piezo-crystal are used to produce the vibrations and to scan the vibrations.

A method is known from DE-A-41 00 338 in which the degree of the filling of the vessel with the free-flowing product is ascertained by measuring the frequency of the mechanical sound vibrations of the vessel housing by a sensor fitted directly onto the vessel wall.

A method is known from DE-A-197 11 093 (=EP 0 831 308 A) in which the contents of a liquefied gas bottle are determined by directing a sound signal onto the gas bottle by means of a sound transmitter placed against the outside of the gas bottle, recording the sound signal given off by the gas bottle, and comparing both signals. The transmitted signal passes through a substantial frequency range and the resonance frequency is established by measuring the amplitude of the received signal.

A method is known from WO 94/24526 in which even ultrasonic waves are produced in a liquid sample in a vessel and the dependence on frequency of the amplitude and/or the phase of the resonances are measured.

In the earlier application DE-A-196 46 685 (=WO 98/21557) which is still not published, a method for determining the fill level of closed vessels is described, primary mechanical vibrations being excited in a vessel wall and the secondary vibrations which are excited by the primary mechanical vibrations of the vessel wall inside the vessel and occur inside the space between the closure and the liquid then being analyzed. The fill level can be ascertained from the frequency of these secondary vibrations.

In the earlier application DE-A-197 36 869 (=WO 99/10722) which is still not published, a method for testing the residual air volume of vessels, which are sealed by a closure is described. The liquid for expulsion of the residual air volume is foamed in the vessels before sealing. The residual air volume is ascertained by exciting mechanical vibrations in the closure which are analyzed directly after the closure is attached, before a major change in the internal pressure takes place in the vessel. The frequency, the decay time, the vibration amplitude and/or the time integral of the vibration amplitude are included in the vibration analysis.

The object of the invention is to determine the fill level of vessels, in particular cans, in as easy and rapid a manner as possible.

This object is achieved according to the invention in that the vibration is produced in a vessel wall which is contacted by the contents to an extent which varies depending on the fill level and in that recorded vibrations are then analyzed to discover to what extent the vessel wall is contacted on the inside by the contents, this including the evaluation of the decay time, the frequency, the intensity and/or the time integral of the intensity or the ascertaining of the site of the maximum intensity of the mechanical vibration.

The mechanical vibrations in the vessel wall are produced in known manner by a short magnetic pulse emanating from a magnetic coil. The magnetic pulse briefly deflects the vessel wall and the vessel wall vibrates back after the magnetic pulse has ended. The mechanical vibration of the vessel wall produces acoustic vibrations, which, for their part, can be received by a microphone, magnetic recorder or the like. This measuring technique has long been known in connection with the determination of the internal pressure of vessels. These mechanical vibrations decay with a certain time constant. The time constant is relatively small, i.e. the attenuation is great when the vessel is full. The lesser the contents, the greater the time constant of the vibration. The fill level has a particularly significant effect on the vibration attenuation.

The increased attenuation also has an effect on the time integral of the vibration amplitude. This time integral is proportional to the area under the curve representing the vibration in a diagram showing the vibration amplitude over time. The smaller this area, the higher the fill level.

In addition, shifts in the vibration frequency also result which can likewise be evaluated. It is generally the case that the frequency becomes higher as the fill level rises.

Because the mechanical vibrations are produced without contact e.g. by a magnetic pulse, in the vessel wall and the vibrations are also recorded without contact, the method according to the invention is suitable in particular for ascertaining the fill level of vessels which are conveyed along a conveyor belt or other transport device.

In a preferred version of the invention, the vibrations of the vessel wall are recorded by two microphones arranged at a distance one above the other and the site of the sound source is ascertained by a comparison of the vibration phases. This exploits the fact that the vibrations in the vessel wall are markedly attenuated below the surface of the liquid, so that it is principally the part of the vessel wall lying above the surface of the liquid that vibrates, so that the centre of the vibrations produced in the vessel shifts upwards as the fill level rises. Information about the fill height can therefore also be obtained by locating the sound source.

The distance between magnetic coil and vessel as well as between vessel and microphone does not play a major role in the evaluation of the vibration with regard to attenuation and frequency. These two distances must however be taken into account when the vibrations are evaluated with regard to the time integral of the amplitude, as here the absolute intensity of the vibration affects the measurement result. Therefore, the distance between magnetic coil and vessel wall and between vessel wall and microphone are preferably taken into account in the evaluation of the vibration with regard to the time integral of the intensity or amplitude. The distance can be measured in known manner by a laser beam, inductively or by ultrasound.

Due to wave motions and sloshing effects of the liquid in the vessel, measurement inaccuracies result. To improve the measurement accuracy, several measuring devices are therefore preferably linked, each measuring device consisting of a magnetic coil and one or two microphones. As the costs of individual measuring devices are relatively low, a clear improvement in the accuracy can be achieved by a larger number, e.g., 10 or more, of measuring devices and the formation of the average value from the results of all measuring devices. Not only the inaccuracy caused by the sloshing of the liquid, but also the inherent measuring inaccuracies of the system, is reduced by a larger number of measuring devices. The measuring devices can thus be arranged on both sides of the vessel or the can.

Figure 2:
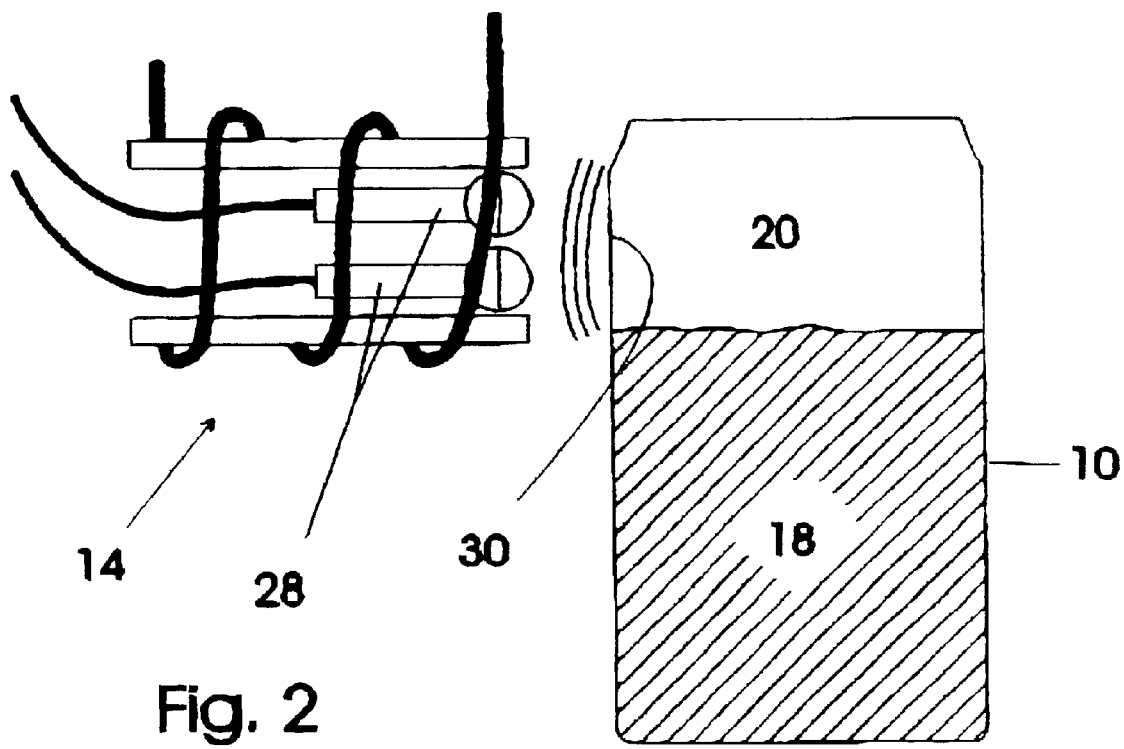
Figure 3:
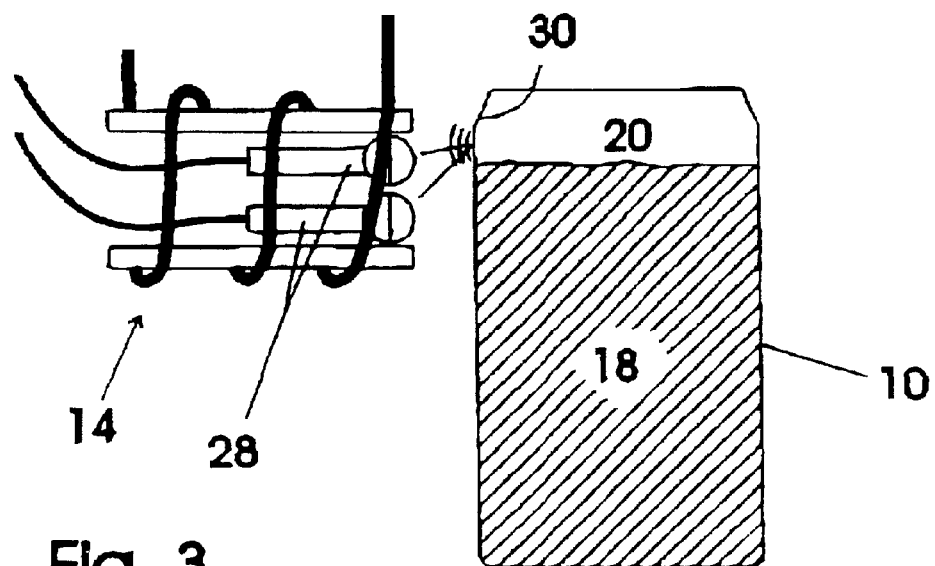

Embodiments of the invention are explained in the following using the drawing. It is shown in:

FIG. 1 an arrangement for producing mechanical vibrations in a can and for receiving the acoustic signals produced by these vibrations;

FIG. 2 an arrangement similar to FIG. 1, but with two microphones for determining the centre of the acoustic vibrations in the case of underfilling and FIG. 3 the arrangement of FIG. 2 with the can normally filled.

In the embodiments shown in the Figures, cans 10 are advanced on a conveyor 12 past a measuring device 14. In FIG. 1, the cans are also guided by fixed side-rails 16. The cans 10 are partly filled with liquid 18 and an air space 20 is located above the liquid.

The measuring device 14 consists of a magnetic coil 22 and a core 24, which has an axial recess 26. Located in the recess 26 are one or two microphones 28. Short electric pulses can be applied to the magnetic coil 22 by means of a source of current, not represented, so that the magnetic coil emits corresponding short magnetic pulses. The measuring device 14 is arranged at the smallest distance possible from a side wall of the passing cans 10 and the magnetic coil 22 is controlled so that it emits the magnetic pulse when the distance from a passing can 10 is at its smallest. The side wall 30 of the can 10 is thereby deflected for a short period towards the magnetic coil 22, as a result of which a mechanical vibration, which very rapidly decays again, is impacted in the side wall 30. The measuring device 14 is arranged at roughly the height of the liquid level when the cans 10 are filled normally.

The vibrations impacted by the magnetic pulse are recorded by the microphone(s) 28 as acoustic vibrations and evaluated by an evaluation device, not represented.

The measuring device 14 with the magnetic coil 22 and the microphones 28 is only schematically represented in the Figures. The magnetic coil 22 can actually have any customary shape, e.g. pot shape or horseshoe shape, by which the magnetic field is concentrated on the side directed towards the cans 10.

The decay time of the mechanical vibrations depends on the fill level. The higher the fill level in the can 10, the shorter the decay time. The vibration signal received by the microphones 28 is evaluated in the evaluation device. By means of customary electronic evaluation devices, the decay time of the vibration can be ascertained. A table of values can be compiled by means of some test runs with cans 10 filled to different levels, and this can then be used to read off the fill level from the decay time.

Likewise, the frequency of the impacted mechanical vibration changes depending on the fill level, so that the fill level can also be read off from the ascertained frequency of the mechanical vibration using a corresponding table of values.

The intensity of the vibration also depends on the fill level, so that information about the fill level can also be provided by its measurement. As the intensity also depends, however, on the distance of the magnetic coil 22 and the microphone 28 from the can 10, the measured intensity value must firstly be adjusted using these distances and standardized. The distance can be measured e.g. by means of transit time measurement of a laser beam.

Finally, the time integral of the amplitude or intensity of the impacted mechanical vibration also very clearly depends on the fill level. Here, too, there must be an adjustment reflecting the distance of the measuring device 14 from the can 10.

There are two microphones 28 present in the embodiment shown in FIGS. 2 and 3. The direction from which the acoustic signal comes can be established by a phase comparison of the vibration signals recorded by the two microphones 28 and the site within the side wall 30 of the can 10 from which the strongest acoustic signal starts can be ascertained, taking into account the distance of the can 10 from the measuring device 14. It transpired that the impacted mechanical vibration has its greatest intensity and amplitude roughly in the middle of the section of the side wall 30 which lies above the fill level. By using two microphones 28, this site of the strongest intensity of the mechanical vibrations can therefore be established and the fill level can be ascertained therefrom, taking into account the overall height of the cans 10.

What is claimed is:

1. Method for ascertaining the fill level of a vessel (10), wherein mechanical vibrations are produced without contact in a vessel wall (30), the produced mechanical vibrations are recorded without contact and the recorded vibrations are analyzed, characterized in that:
   the mechanical vibrations are produced by a short, magnetic pulses deflected from the vessel wall (30) which is contacted by the contents to an extent which varies depending on the fill level, and
   the recorded vibrations are then analyzed to discover to what extent the vessel wall (30) is contacted on the inside by the contents, this including evaluation of the decay time, the frequency, the intensity, and/or the time integral of the intensity, or the ascertaining of the maximum intensity of the mechanical vibration.

2. Method according to claim 1, characterized in that to ascertain the site of the maximum intensity of the mechanical vibrations, the mechanical vibrations are recorded by two microphones arranged at a distance from each other and the vibration phases of the vibrations recorded by each microphone are compared.

3. Method according to claim 1, characterized in that the fill level in a vessel (10) is ascertained several times and the average value of the ascertained fill levels is formed.

4. Method according to claim 1, characterized in that the mechanical vibration is produced at a point on the vessel wall (30) which is roughly at the height of the normal fill.

5. Method according to claim 1, characterized in that during the analysis of the recorded vibrations with regard to the time integral of the intensity or amplitude the distance between the device for producing the mechanical vibrations and the vessel wall and the distance between the vessel wall and the device for recording the vibrations are taken into account.

6. Method according to claim 5, characterized in that the distance is measured by means of a laser beam, inductively, or by ultrasound.

7. Device for carrying out the method of claim 1, with a device (22) for producing mechanical vibrations in the vessel wall (30) and with a device (28) for recording and evaluating the mechanical vibrations, characterized in that, the devices (22, 28) for producing mechanical vibrations in the vessel wall (30) has a magnetic coil which is arranged such that it can by means of a magnetic pulse bring about a short period of deflection in the side wall of a passing vessel for producing the mechanical vibrations.

* * * * *